(12) United States Patent
Kuwana et al.

(10) Patent No.: US 8,216,838 B2
(45) Date of Patent: Jul. 10, 2012

(54) METHOD FOR EFFICIENT PRODUCTION OF MONOCYTE-DERIVED MULTIPOTENT CELL (MOMC)

(75) Inventors: Masataka Kuwana, Tokyo (JP); Takashi Kato, Tokyo (JP); Noriyuki Seta, Tokyo (JP); Hiroshi Miyazaki, Tokyo (JP)

(73) Assignee: Keio University, Tokyo (JP)

( * ) Notice: Subject to any disclaimer, the term of this patent is extended or adjusted under 35 U.S.C. 154(b) by 120 days.

(21) Appl. No.: 12/738,997

(22) PCT Filed: Oct. 22, 2008

(86) PCT No.: PCT/JP2008/002990
§ 371 (c)(1),
(2), (4) Date: Apr. 27, 2010

(87) PCT Pub. No.: WO2009/054128
PCT Pub. Date: Apr. 30, 2009

(65) Prior Publication Data
US 2010/0261202 A1    Oct. 14, 2010

(30) Foreign Application Priority Data

Oct. 23, 2007  (JP) .................................. 2007-275461

(51) Int. Cl.
*C12N 5/08* (2006.01)
*C12N 5/00* (2006.01)

(52) U.S. Cl. ....................................... 435/372; 435/375
(58) Field of Classification Search ........................ None
See application file for complete search history.

(56) References Cited

U.S. PATENT DOCUMENTS

| 7,101,708 B1 | 9/2006 | Lapidot et al. |
| 2008/0014214 A1* | 1/2008 | Krathwohl ................ 424/198.1 |

FOREIGN PATENT DOCUMENTS

| EP | 1 605 040 A1 | 12/2005 |
| GB | 2 426 765 A1 | 12/2006 |
| JP | 2004-275145 | 10/2004 |
| JP | 2006-333866 | 12/2006 |

OTHER PUBLICATIONS

Takahashi et al., Eur. J. of Pharmacology, 2006, v.552 pp. 162-169.).*
Seta et al., "Investigation on the Induction Process of Human Monocyte-Derived Multipotent Cell," Inflammation and Regeneration, p. 334 Jul. 1, 2007.
Seta et al., "Identification of Molecular Factors Required for Transdifferentiation of Human Circulating Monocytes into Multipotential Cells," Blood, pp. 710-711, #2408, Nov. 16, 2007.
Kodama et al., Cardiomyogenic Potential of Mesenchymal Progenitors Derived from Human Circulating $CD14^+$, *Monocytes, Stem Cells and Development*, vol. 14, pp. 676-686, 2005.
Kodama et al., Neurogenic potential of progenitors derived from human circulating $CD14^+$ monocytes, *Immunology and Cell Biology*, vol. 84, pp. 209-217, 2006.
Kuwana et al., Human circulating $CD14^+$ monocytes as a source of progenitors that exhibit mesenchymal cell differentiation, *Journal of Leukocyte Biology*, vol. 74, pp. 833-845, Nov. 2003.
Kuwana et al., Endothelial Differentiation Potential of Human Monocyte-Derived Multipotential Cells, *Stem Cells*, vol. 24, pp. 2733-2743, 2006.
Tashiro et al., Signal sequence trap: a cloning strategy for secreted proteins and type I membrane proteins, *Science*, vol. 261(5121), pp. 600-603, Jul. 30, 1993.
Seta et al., "Human Circulating Monocytes as Multipotential Progenitors," The Keio Journal of Medicine, 56(2), pp. 41-47, Jun. 2007.
Extended European Search Report for European Application No. 08843082.2, in the name of Keio University, Dec. 19, 2011, 7 pages.

* cited by examiner

*Primary Examiner* — Michail Belyavskyi
(74) *Attorney, Agent, or Firm* — Kenneth H. Sonnenfeld; Margaret B. Brivanlou; King & Spalding

(57) ABSTRACT

It is to provide a practical method for producing efficiently a large amount of MOMC, which is a multipotent cell which is very suitable for cell transplantation for organ regeneration. It was found that by culturing peripheral blood monocytes in vitro on fibronectin in the presence of SDF-1, MOMC can be produced more efficiently, and the present invention has been completed. Specifically, it is a method for producing MOMC by culturing in vitro peripheral blood monocytes expressing CD14 on fibronectin, wherein the in vitro culture is performed in the presence of SDF-1.

1 Claim, 16 Drawing Sheets

Fig. 1
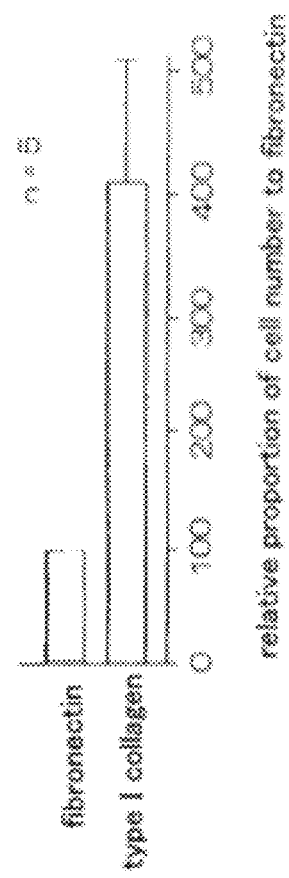
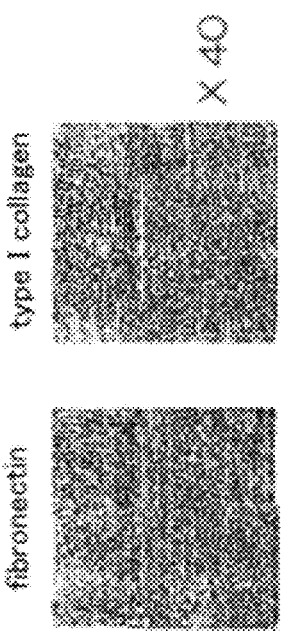
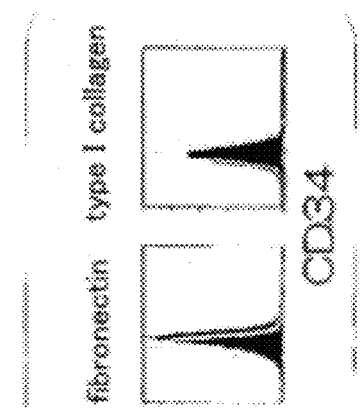

Fig. 3

β1 integrin family (VLA-1 ~ 6)

| VLA | α | β | expressed cells | ligands |
|---|---|---|---|---|
| VLA-1 | α1/CD49a | β1 | monocytes, T cells, vascular endothelial cells, fibroblast cells | type I collagen, laminin |
| VLA-2 | α2/CD49b | β1 | platelets, monocytes | type I collagen, laminin |
| VLA-3(/) | α3/CD49c | β1 | vascular endothelial cells, T cells | fibronectin, type I collagen, laminin |
| VLA-4 | α4/CD49d | β1 | monocytes, T cells | fibronectin, VCAM-1 |
| | | β7 | monocytes, T cells | fibronectin, VCAM-1, MadCAM-1 |
| | | β1 | monocytes, platelets, vascular endothelial cells | fibronectin |
| VLA-5 | α5/CD49e | β1 | platelets, monocytes, T cells | laminin |
| VLA-6 | α6/CD49f | β4 | platelets, monocytes, T cells | laminin |

Fig. 5
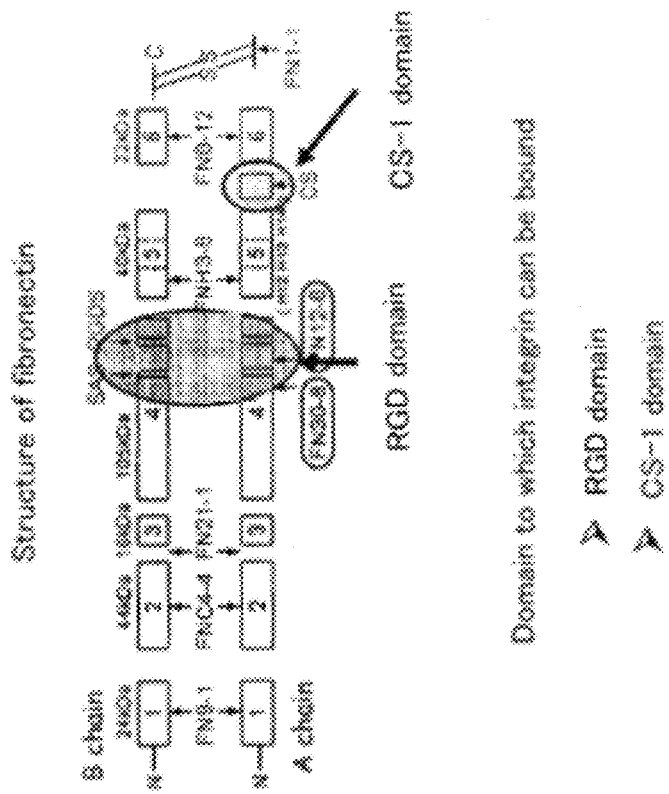
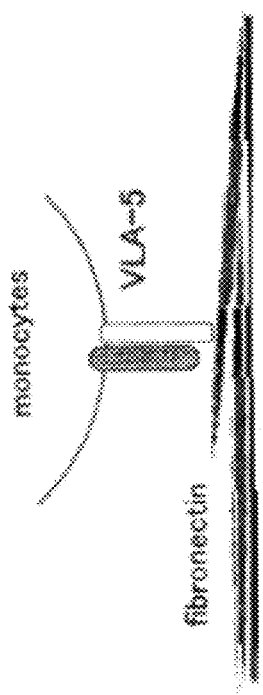

Fig. 7
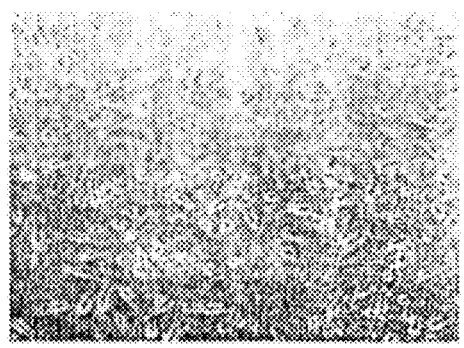
A)
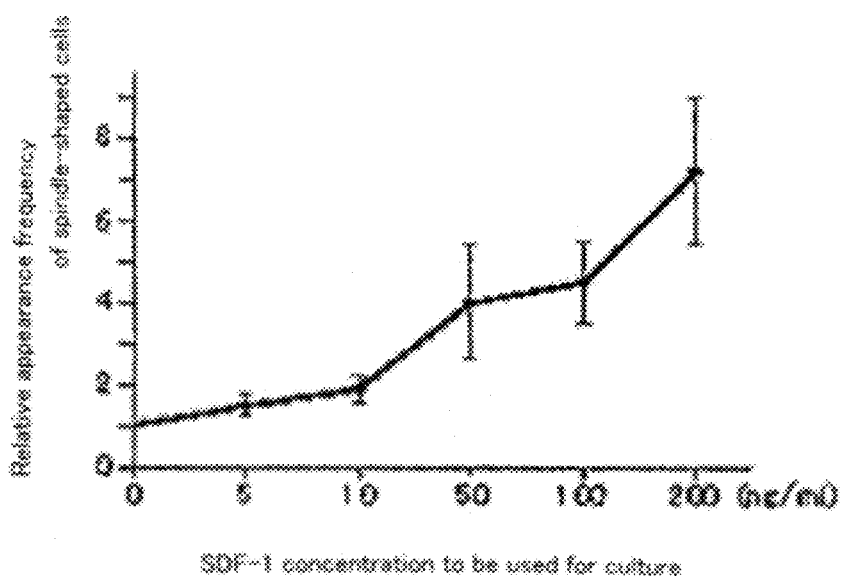
B)

Fig. 9
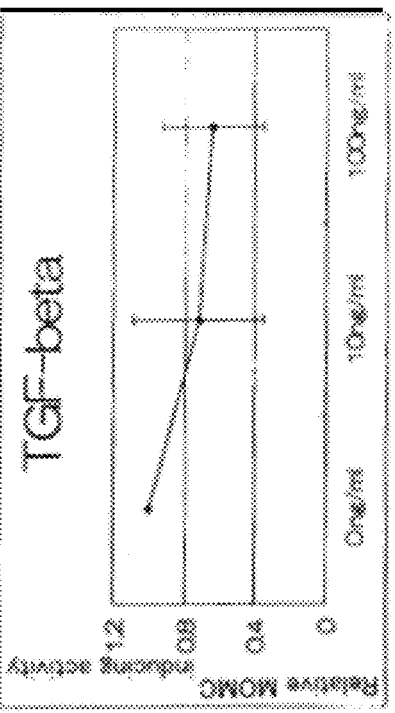
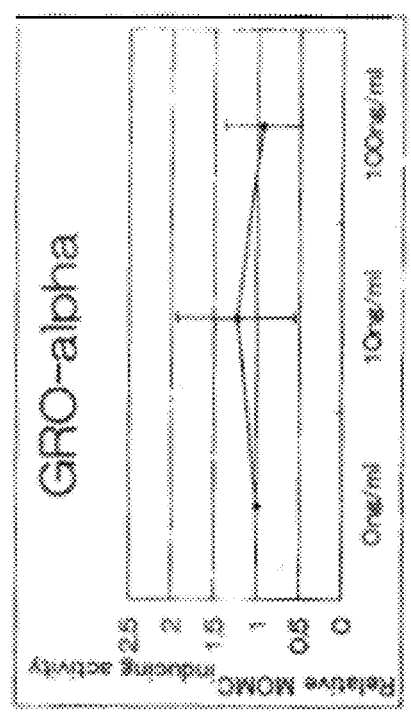
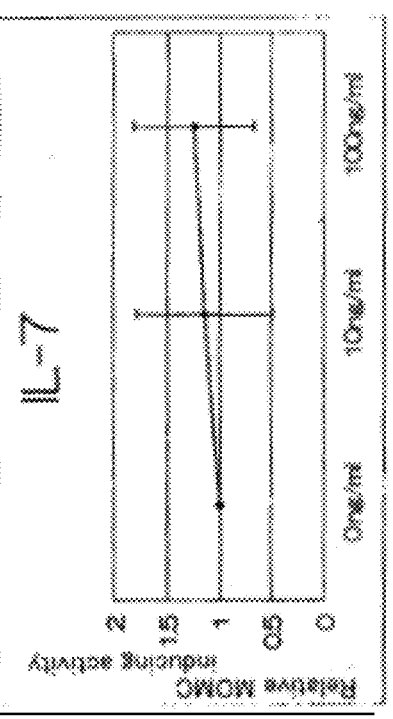
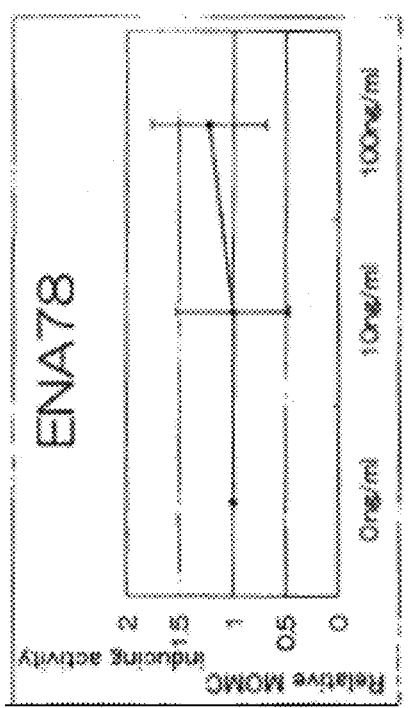

Fig. 10
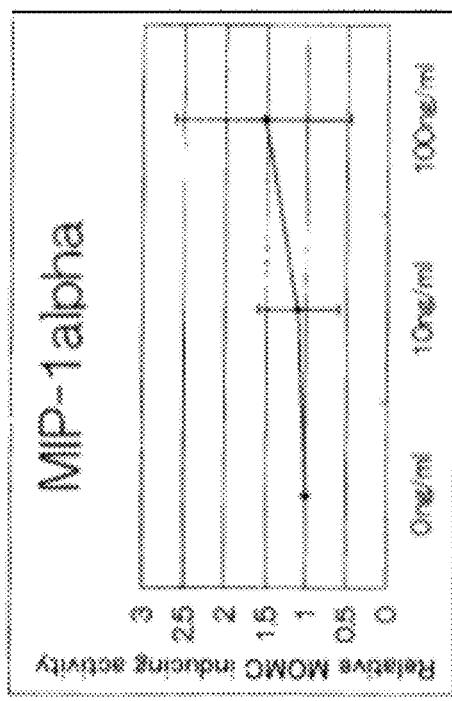
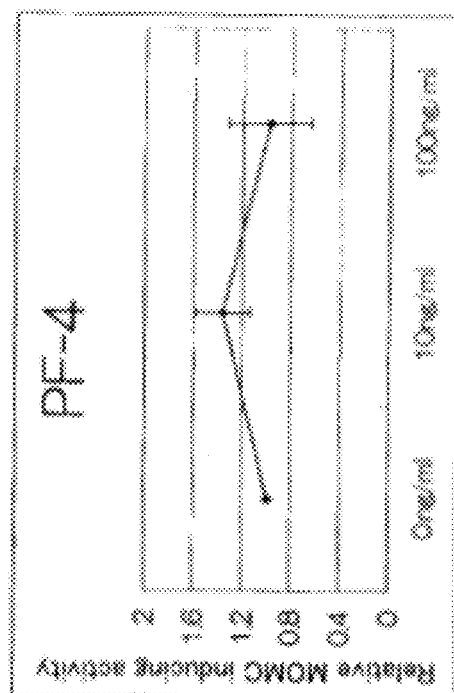
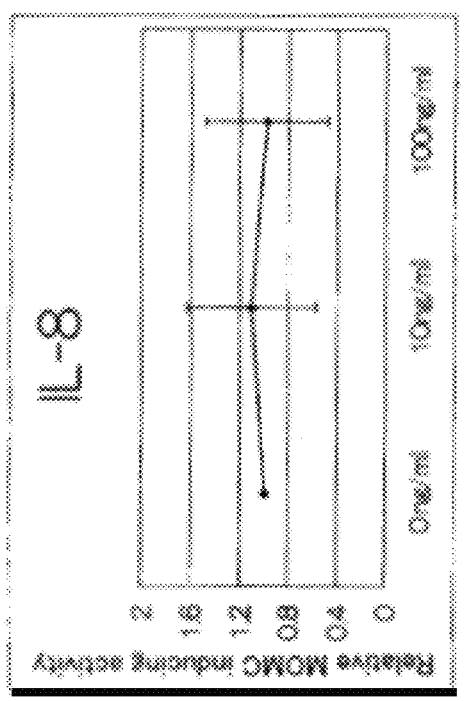
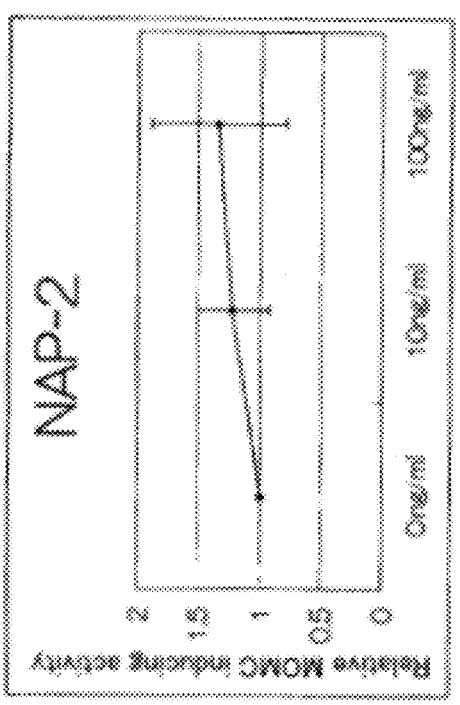

Fig. 11
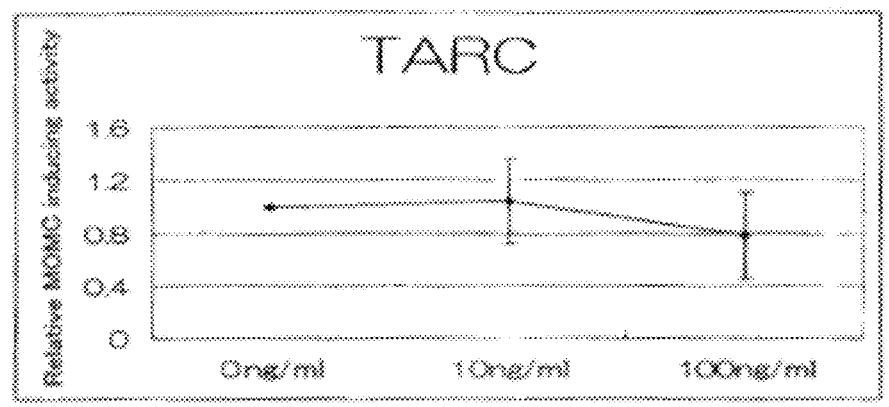
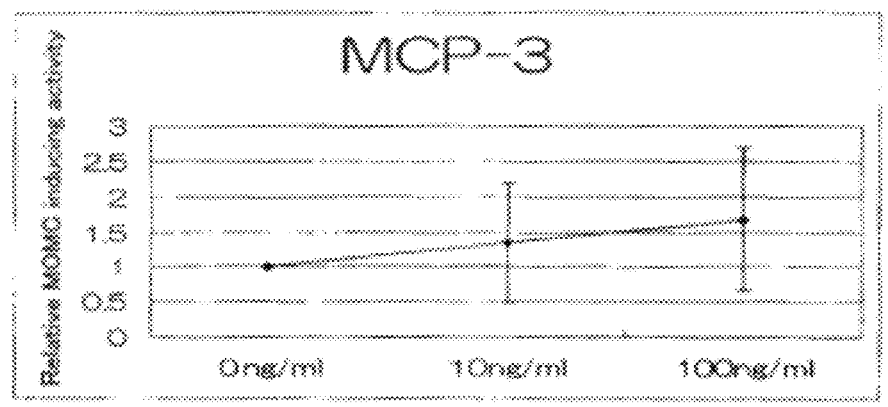
Fig. 12
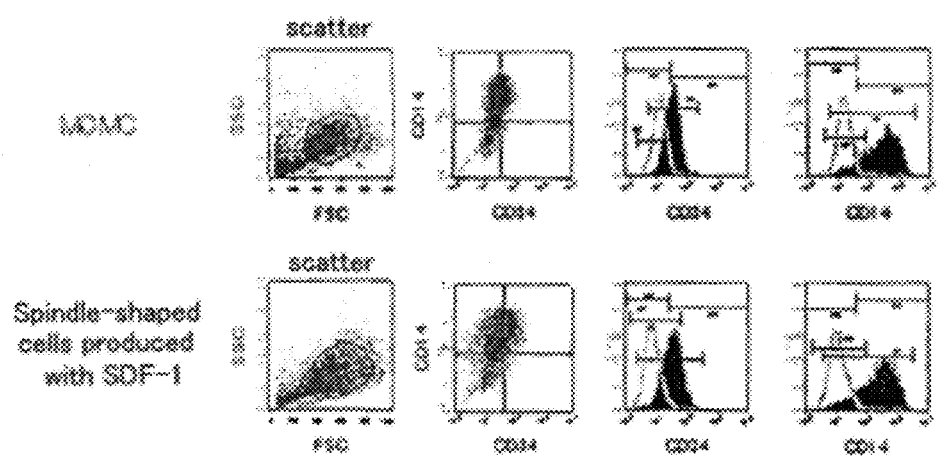

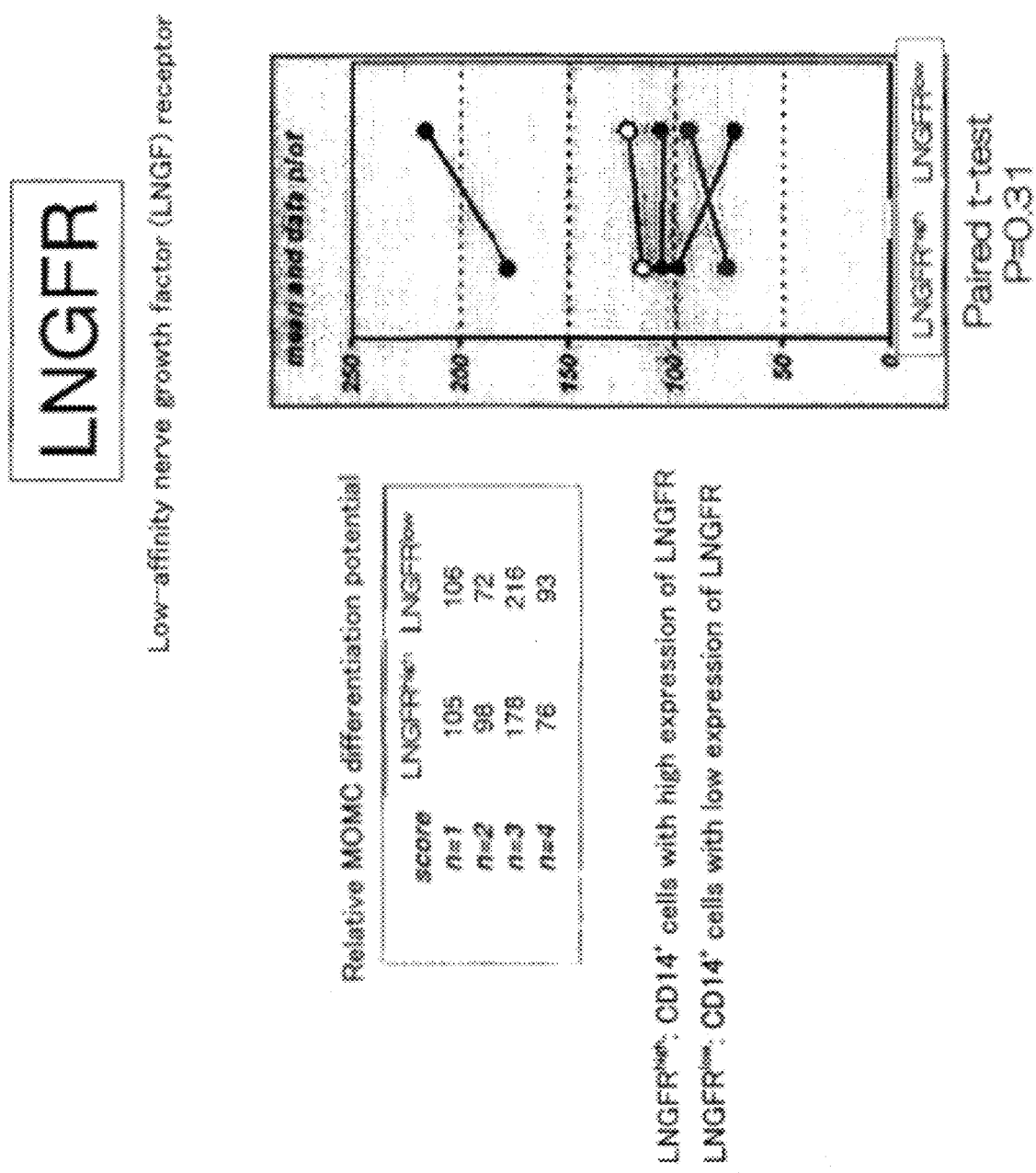

SEQUENCE LISTING

```
<160> NUMBER OF SEQ ID NOS: 4

<210> SEQ ID NO 1
<211> LENGTH: 6
<212> TYPE: PRT
<213> ORGANISM: Homo sapiens

<400> SEQUENCE: 1

Gly Arg Gly Asp Ser Pro
1               5
```

```
<210> SEQ ID NO 2
<211> LENGTH: 5
<212> TYPE: PRT
<213> ORGANISM: Homo sapiens

<400> SEQUENCE: 2

Glu Ile Leu Asp Val
1               5

<210> SEQ ID NO 3
<211> LENGTH: 6
<212> TYPE: PRT
<213> ORGANISM: Homo sapiens

<400> SEQUENCE: 3

Gly Arg Gly Glu Ser Pro
1               5

<210> SEQ ID NO 4
<211> LENGTH: 5
<212> TYPE: PRT
<213> ORGANISM: Homo sapiens

<400> SEQUENCE: 4

Glu Ile Leu Ala Val
1               5
```

METHOD FOR EFFICIENT PRODUCTION OF MONOCYTE-DERIVED MULTIPOTENT CELL (MOMC)

TECHNICAL FIELD

The present invention relates to a method for producing a monocyte-derived multipotent cell (MOMC), and to an agent for inducing differentiation into MOMC.

BACKGROUND ART

The big problem remaining in modern medicine is said to overcome deficiency of organs due to disease or external injuries, and functional impairment. The only method that can be practiced today for treating such condition is organ transplantation. However, there are still many difficulties for spreading as an actual therapeutic method, due to problems such as brain-death diagnosis or supply from donors. On the other hand, regenerative medicine intending regeneration of organs draws attention with the recent development of stem cells and developmental biology, and is expected as the direction of the medicine to advance in the 21st century. In animal experiment level, functional recoveries of organs by transplantation of embryonic stem cells (ES cells) have been reported, while at present, the application in human is coming up against a brickwall due to rejection or ethical problems of the use of ES cells. Further, as various adult tissue stem cells (mesenchymal, blood vessels, liver etc.) are extremely few in vivo, the isolation thereof is technically difficult, and it is hard at the present time to obtain sufficient amount of cells for transplantation. Therefore, there are many problems to be solved before the regenerative medicine using ES cells or tissue stem cells can be applied to the actual medicine. Particularly, it is essential to have a stable supply of cells having differentiation potential so that regenerative medicine by cell transplantation becomes a reality.

The present inventors have found first in the world, that human peripheral blood monocyte-derived cells have a potential to differentiate into bone, cartilage, skeletal muscle, fat, cardiac muscle, vascular endothelial and neurons under a particular culture condition (nonpatent documents 1 to 4, patent document 1), and have named this novel cell as monocyte-derived multipotent cell (MOMC). As monocytes can be easily collected from peripheral blood largely non-invasively, it can be obtained in a relatively simple manner. Further, as it represents about 20% of peripheral blood mononuclear cells, cells can be provided stably in a necessary and sufficient amount. Further, as MOMC can be produced from monocytes from a subject to be administered, there are no problems for securing donors or of rejection, and there are almost no ethical problems. Specifically, it can be said that MOMC is a multipotent cell that is very suitable for cell transplantation, for actual organ regeneration. Patent Document 1 filed by the present inventors describes a method for producing MOMC by inducing differentiation of peripheral blood monocytes into MOMC by using CD14$^-$ cells. By utilizing the present method, differentiation induction from monocytes into MOMC can be conducted simply, rapidly and at a low cost, without using a particular device. Further, the present inventors have previously found that it is necessary to coculture with platelets and not with lymphocytes for inducing MOMC from peripheral blood monocytes (Nonpatent Document 5).

On the other hand, Patent Document 2 discloses a method for forming P stem cells comprising transforming mononuclear cells to P stem cells with protein kinase C bII of activated mononuclear cell, and also describes to use GM-CSF, SDF or a combination thereof as protein kinase C conditioner. Patent document 2 further describes that P stem cell can be differentiated into cartilage cells, neurons or osteocytes. Moreover, P stem cell is a cell that can be obtained by a culture on either collagen or fibronectin (see "specific example 3 of Example 1" of Patent Document 2).

Moreover, SDF-1 (Stromal Derived Factor 1) is one kind of cytokine that performs growth, differentiation and functional expression of cells (nonpatent document 6). Cytokines include a large variety of proteins, and the followings are well known: interleukin (IL), colony stimulating factor (CSF), stem cell factor (SCF), tumor necrosis factor (TNF), interferon (IFN), transforming growth factor (TGF), bone morphogenic protein (BMP), epidermal growth factor (EGF), keratinocyte growth factor (KFG), fibroblast growth factor (FGF), insulin-like growth factor (IGF), platelet-derived growth factor (PDGF), hepatocyte growth factor (HGF), vascular endothelial growth factor (VEFG), macrophage inflammatory protein (MIP), monocyte chemotactic protein (MCP), and RANTES. Among these, those that have been found as a series of cytokines dominating the migration activity and activation of a specific leukocyte subset are particularly called chemokines. Chemokines contain conserved cysteine residues (Cys) in the molecule, and are classified into four subfamilies (CXC, CC, C, CX3C) based on their position in the molecule structure. SDF-1 is a CXC-type chemokine, and SDF-1 receptor is known to be CXCR4, which is one of the CXC chemokine receptors.

As it is stated in the above, the method for producing MOMC was known from patent document 1, while a more useful method for producing MOMC with a higher MOMC differentiation efficiency was awaited. However, it has not been known at all whether SDF-1 affects the differentiation-inducing efficiency from peripheral blood monocytes into MOMC.

Patent Document 1: Japanese Patent No. 3762975
Patent Document 2: Japanese Published Patent Application No. 2006-333866
Nonpatent Document 1: J Leukoc Biol, 2003, 74, 833-45
Nonpatent Document 2: Stem Cell Dev, 2005, 14, 676-86
Nonpatent Document 3: Immunol Cell Biol, 2006, 84, 209-17
Nonpatent Document 4: Stem Cells, 2006, 84, 2733-43
Nonpatent Document 5: The Japanese Society of Inflammation and Regeneration, Abstracts W-7-4, "Investigation on the induction process of human monocytes derived-multipotent cells", Published on July 2007
Nonpatent Document 6: Science, 1993, 261, 600-603

DISCLOSURE OF THE INVENTION

Problem to be solved by the Invention

The object of the present invention is to provide a useful method for producing MOMC, which is a multipotent cell being very suitable for cell transplantation for organ regeneration, with high efficiency, and in a large amount.

Means to solve the Problem

The present inventors had knowledge that it is necessary to coculture with platelets and not with lymphocytes for inducing MOMC from peripheral blood monocytes (nonpatent document 5). Thus, they searched for substances having differentiation-inducing activity into MOMC among a large number of cytokines known to be produced by platelets. However, no substance having the intended activity was found. Thus, they made a keen study by expanding the subject of the search to cytokines, etc. released with platelet activation, even not produced by platelets. They finally found out that by using SDF-1, MOMCs can be efficiently produced from peripheral blood monocytes. The present invention has been thus completed.

Specifically, the present invention relates to (1) a method for producing monocyte-derived multipotent cell (MOMC) comprising culturing in vitro a peripheral blood monocyte expressing CD14 on fibronectin, wherein the in vitro culture is performed in the presence of SDF-1; (2) the method for producing MOMC according to (1), further comprising using a monocyte highly expressing CXCR4 as peripheral blood monocyte expressing CD14.

Further, the present invention relates to (3) an agent for promoting differentiation induction into monocyte-derived multipotent cell (MOMC) comprising SDF-1 as active ingredient.

Moreover, the present invention relates to (4) a method for screening a substance promoting differentiation induction into monocyte-derived multipotent cell (MOMC), comprising a step of measuring a CXCR4 expression level in a monocyte obtained by culturing peripheral blood monocyte expressing CD14 in the presence of a test substance; and a step of assessing the CXCR4 expression level obtained by measurement.

BRIEF DESCRIPTION OF THE DRAWINGS

FIG. 1 It is a figure showing the results of comparative examination on MOMC differentiation potential of type I collagen and fibronectin.

FIG. 3 It is a figure showing the types of integrin family being adhesion molecules, and their property.

FIG. 5 It is a figure showing the structure of fibronectin.

FIG. 7 It is a figure showing the MOMC-like spindle-shaped cells which have appeared by a culture using SDF-1, and that the appearance frequency increases depending on the concentration of the added SDF-1.

FIG. 9 It is a figure showing the investigation results on MOMC inducing activity of IL-7, TGF-β, ENA78, and GRO-α.

FIG. 10 It is a figure showing the investigation results on MOMC inducing activity of IL-8, MIP-1α, NAP-2, and PF-4.

FIG. 11 It is a figure showing the investigation results on MOMC inducing activity of MCP-3 and IARC.

FIG. 12 It is a figure showing the comparison results of the CD14 and CD34 expressions in MOMC-like spindle-shaped cells produced by SDF-1 with the expressions in MOMC produced by a conventional method.

FIG. 19 It is a figure showing the results of comparative examination on differentiation efficiency of CD14$^+$LNGFR$^{low}$ cells and CD14$^+$LNGFR$^{high}$ cells into MOMC.

BEST MODE OF CARRYING OUT THE INVENTION

Figure 2:
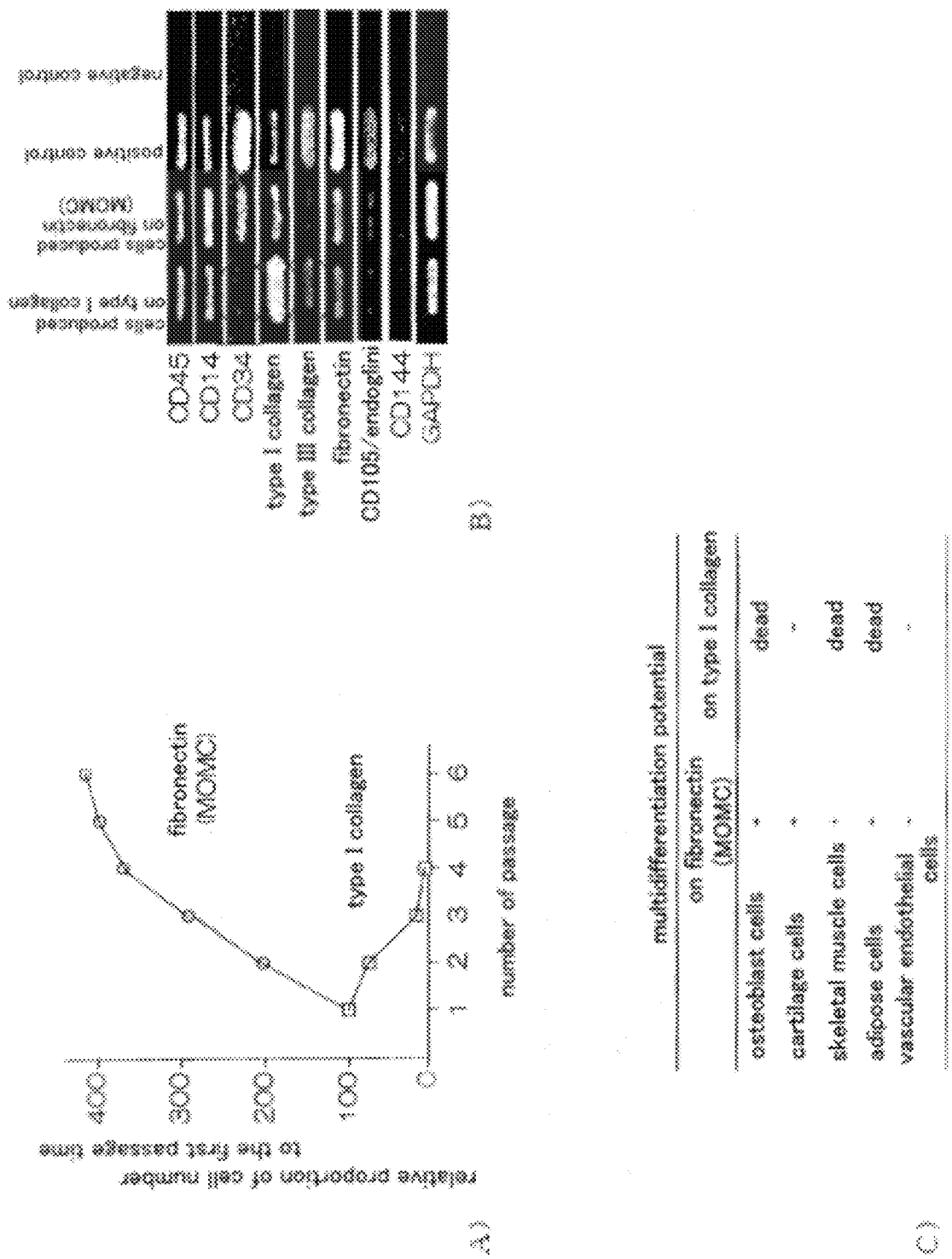
FIG. 2 It is a figure showing the results of comparative examination on MOMC differentiation potential of type I collagen and fibronectin.

The method for producing monocyte-derived multipotent cell (MOMC) of the present invention (hereinafter also referred simply as to "the production method of the present invention") is a method for producing MOMC by culturing in vitro peripheral blood monocytes expressing CD14 on fibronectin, wherein the in vitro culture is performed in the presence of SDF-1. Herein, in the presence of SDF-1 means to add SDF-1 or a composition containing SDF-1 to the medium used in the in vitro culture. It is preferred to add SDF-1 to the medium, as the SDF-1 concentration can be specifically increased according to need. The concentration of SDF-1 in the medium is not particularly limited, while it is preferably 10 to 200 ng/ml, and more preferably 50 to 200 ng/ml.

The origin of the peripheral blood monocytes expressing CD14 (hereinafter referred to as "CD14-positive peripheral blood monocyte") is not particularly limited, and examples include mouse, rat, dog, pig, monkey and human, and human is preferred. As for human monocyte, it can be a monocyte from a donor, while an autologous one is particularly preferred. These peripheral blood monocytes can be isolated by common methods from venous blood of the animal to be the origin. Further, the method for separating the CD14-positive peripheral blood monocytes from peripheral blood monocytes is not particularly limited, and CD14-positive peripheral blood monocytes can be easily separated from peripheral blood monocytes, for example by using anti-CD14 antibody binding magnetic beads.

As CD14-positive peripheral blood monocytes used in the present invention, it is more preferred to use CD14-positive peripheral blood monocytes highly expressing CXCR4. Specifically, it is preferred to use the top 70% monocytes in which expression number of CXCR4 is large among the collected CD14-positive peripheral blood monocytes, and more preferred to use the top 50% monocytes. The expression number of CXCR4 can be easily measured by for example using labeled anti-CXCR4 antibody and flow cytometry, and monocytes in which expression number of CXCR4 is high can be selected.

Further, the method of the above-mentioned in vitro culture is not particularly limited as long as it is a method to culture CD14-positive peripheral blood monocytes in vitro in the presence of SDF-1 on fibronectin. However, the following method can be suitably exemplified: a method of culturing CD14-positive peripheral blood monocytes on a fibronectin-coated plastic plate in the presence of SDF-1 at 37° C., with 5% $CO_2$ in a humidified atmosphere, at a density of $10^4$ to $10^7$/ml, for example at $2\times10^6$/ml, and depleting non-adherent cells and supplementing a fresh medium every 2 to 4 days, particularly preferably every 3 days, preferably for 5 to 14 days, and particularly preferably for 7 to 10 days, and collecting MOMC. Thus obtained MOMCs of the present invention can be proliferated in culture by maintaining their original phenotype for up to 5 passages.

The medium used in the above-mentioned in vitro culture is not particularly limited as long as it is a medium for culturing cells containing SDF-1, and platelets culture supernatant containing SDF-1 (a low glucose Dulbecco's modified Ealge's medium (DMEM) supplemented with 10% fetal bovine serum (FBS)) can be suitably exemplified. SDF-1 used in the present invention is not particularly limited, and a commercialized product can be used. As for the source of SDF-1, it is preferred to use SDF-1 of the same species as the source according to the source of CD14-positive peripheral blood monocytes to be cultured, and for example, it is preferred to use human-derived SDF-1 when using human-derived CD14-positive peripheral blood monocytes.

Further, the medium can contain other optional components such as cytokines other than SDF-1, as long as differentiation induction into MOMC can be performed. A medium containing cytokines having an activity to inhibit induction into MOMC, such as TGF-β, PDGF-AA, PDGF-AB and bFGF, as cytokines other than SDF-1 can be used. However, it is preferred that the concentration of any one or more of these cytokines in the medium is 1 ng/ml or less, more preferably 100 pg/ml or less, even more preferably 10 pg/ml, and further more preferably 1 pg/ml or less.

It can be readily determined whether the cells obtained by the production method of the present invention are MOMCs or not by confirming the following properties of MOMCs.

MOMC is a spindle-shaped cell or cell population derived from monocyte expressing CD14, that expresses CD14, CD34, CD45 and type I collagen. The above CD14 and CD45 are known as a monocyte- or monocyte-derived cell-marker, CD34 as stem cell marker, and type I collagen as mesenchymal cell marker. It is preferred that MOMC of the present invention expresses CD105 and Sca-1 as stem cell marker, type III collagen and fibronectin as mesenchymal cell marker, and VE cadherin and Flt-1 as vascular endothelium marker. Such MOMC is a cell different from monocyte, macrophage or dendritic cell, from the view point of the expression pattern of the above proteins, and it can be said to be a cell population having the properties of mesenchymal cell, vascular endothelium cell and stem cell in combination.

The agent for promoting differentiation induction of the present invention is characterized by containing SDF-1 as active ingredient. By adding the agent for promoting differentiation induction of the present invention to the medium for culturing CD14-positive peripheral blood monocytes in vitro on fibronectin, the induction efficiency into MOMC increases, which enables to produce MOMCs at a lower cost.

The concentration of SDF-1 contained in the agent for promoting differentiation induction of the present invention is not particularly limited as long as it can increase the induction efficiency into MOMC by adding SDF-1 to the above-mentioned medium. Further, the agent for promoting differentiation induction of the present invention can contain only SDF-1, while it can contain an optional ingredient other than SDF-1 as long as it does not inhibit MOMC induction. Examples of such optional ingredients include solvents such as water, culture components of monocytes such as carbon source and nitrogen source, and MOMC differentiation-inducing substances other than SDF-1.

The dosage form of the agent for promoting differentiation induction of the present invention is not particularly limited, and it may be in a solid dosage form such as powder, or a liquid dosage form such as liquid.

The method for screening a substance for promoting differentiation induction into MOMC of the present invention (hereinafter also referred to as "the screening method of the present invention") is characterized by comprising the step (A) of measuring the CXCR4 expression level of a monocyte obtained by culturing peripheral blood monocytes expressing CD14 in the presence of a test substance; and the step (B) of assessing the CXCR4 expression level obtained by the measurement. As CD14-positive peripheral blood monocytes whose CXCR4 expression level is high have a high induction efficiency into MOMC compared to those whose CXCR4 expression level is low, it is assumed that the substance enhancing the CXCR4 expression level promotes also the differentiation induction into MOMC.

The above-mentioned step (A) is not particularly limited as long as it is a step of measuring the CXCR4 expression level of a monocyte obtained by culturing peripheral blood monocytes expressing CD14 (CD14-positive peripheral blood monocytes) in the presence of a test substance. The method for measuring the CXCR4 expression level of monocytes in the above step is not particularly limited, and for example, it can be easily measured by using labeled anti-CXCR4 antibody and flow cytometry.

The above-mentioned step (B) is not particularly limited as long as it is a step of assessing the CXCR4 expression level obtained by measurement. For example, when the CXCR4 expression level of monocytes obtained by culturing CD14-positive peripheral blood monocytes in the absence of a test substance is used as a standard, and the expression level is higher when the culture is performed in the presence of the test substance, it can be assessed that the test substance is a substance promoting differentiation induction into MOMC.

MOMC produced by the above-mentioned production method of the present invention is multipotent. Multipotency of MOMC can be exemplified by the multipotency that enables differentiation into mesodermal cell under the inducing condition which is known to differentiate mesenchymal stem cell (MSC) into mesodermal cells; and more specifically, the followings can be suitably exemplified: multipotency that allows differentiation into mesenchymal cells such as osteoblast cells, skeletal myoblasts, cartilage cells and adipose cells by a culture under a condition inducing differentiation into mesenchymal cells, multipotency that allows differentiation into myocardial cells by a culture under a condition inducing differentiation into cardiac muscle, such as a coculture with cultured myocardial cells; multipotency that allows differentiation into vascular endothelial cells by a culture under a condition inducing differentiation into vascular endothelium, such as a culture under a condition maintaining vascular endothelial cells; as well as multipotency that allows differentiation into neurons that are ectodermal cells, by a culture under a condition inducing differentiation into nerve, such as a coculture with cultured neuron.

By administering MOMCs of the present invention, and/or the mesodermal progenitors, mesodermal cell and/or mesodermal tissues, the neural progenitors, neurons and/or nerve tissues which have been induced to differentiate from MOMCs, for example by injecting them directly to the impaired or defective site, or in the proximity thereof, or by administering them to the peripheral blood, congenital diseases, degenerative diseases or external injury of the above tissues can be treated. It is preferred to determine appropriately either of MOMCs or MOMCs that have been treated for inducing differentiation are suitable as a therapeutic agent, according to the type of cells or diseases, or administering method. Further, as MOMC is a cell to which gene can be introduced relatively easily, it can be used for tissue regenerating therapy, etc. by introducing a particular gene prior to the cell transplantation to human. For example, when there is an impairment to bone formation due to a certain congenital disease, it is possible to transplant MOMC after modifying the gene, or to prepare it so that it generates a particular protein (cytokine, growth factor, hormone, etc.).

As described above, MOMCs of the present invention are very useful as a source of cells for tissue regenerating therapy for the above-mentioned tissues. For instance, as for disease or pathology to be the object of the therapeutic agent or therapeutic method using MOMC of the present invention, examples include osteoclast due to degenerative disease such as dysostosis, fracture and rheumatoid arthritis; rheumatoid arthritis disrupting cartilage or osteoarthrosis, or amyotrophy due to congenital disease such as dystrophy or acquired disease such as myositis; myocardial disease due to myocardial infarction or cardiomyopathy, brain disorder such as brain infarction and Parkinson disease; external injury such as spinal cord damage, or angiopathy due to arteriosclerosis or connective tissue disease. Moreover, aesthetic plastic surgery such as breast augmentation is encompassed in the object of the therapeutic agent or therapeutic method of the present invention for convenience. In cell therapy using MOMCs or MOMCs that have been treated for inducing differentiation, there are considerable advantages over currently proposed regenerative treatment, etc. using tissue-specific stem cells and ES cells. In other words, as a large number of monocytes can be obtained from patients by collecting their blood, a minimally invasive procedure, circulating monocytes could be a relatively easily obtainable source of autologous cells. Furthermore, the generation of MOMCs from monocytes is technically easy and quick, and the ethical dilemma of using ES cells can be bypassed.

In the following, the present invention is explained in detail by referring to the Examples, while the technical scope of the present invention is not limited to these exemplifications.

Example 1

MOMC is a cell having multidifferentiation potential which is induced by culturing CD14-positive peripheral blood monocytes ($CD14^+$ monocytes in peripheral blood) in vitro, which phenotype is $CD14^+CD45^+CD34^+$ type I collagen$^+$. In the conventional method for producing MOMC (Japanese Patent No. 3762975), it was required that $CD14^+$ monocytes adhere to solid-phase fibronectin in the step of inducing differentiation from $CD14^+$ monocytes in peripheral blood into MOMC, and that a liquid factor derived from $CD14^+$ monocytes is present in the culture solution. Further, in Example 19 of the specification of Japanese Patent No. 3762975, it has been revealed that not all of the peripheral blood $CD14^+$ monocytes differentiate into MOMC, but only some of the cells have a differentiation potential. Further, the present inventors have previously found out that it is necessary to coculture with platelets and not with lymphocytes for inducing MOMC from peripheral blood monocytes (non-patent document 5). The present inventors have specified the "adhesion factor" and "liquid factor" essential for MOMC differentiation induction, and investigated the properties of monocytes that are suitable for producing MOMC in order to establish an efficient method for producing MOMC.

Example 2

Identification of Adhesion Factor Associated with MOMC Differentiation Induction First, the MOMC differentiation-inducing potential of fibronectin and type I collagen was compared. Venous blood obtained from healthy adult donor was subjected to density-gradient centrifugation to isolate peripheral blood monocytes (PBMC). Further, $CD14^+$ monocytes were separated from PBMC by using anti-CD14 antibody binding magnetic beads. The obtained $CD14^+$ monocytes were suspended into platelet culture supernatant containing SDF-1 (low glucose Dulbecco's modified Eagle's medium (DMEM) supplemented with 10% fetal bovine serum (FBS)), and cultured on a fibronectin- or type I collagen-coated plate for 7 to 10 days. As a result, in cells obtained from the culture on type I collagen, a significant increase was observed in the number of adhered cells compared to those obtained on fibronectin (FIG. 1A). However, as a result of a flow cytometry analysis, CD34 expression which is one of the characteristic phenotypes of MOMC was not observed (FIG. 1B). Further, while the number of cells cultured on fibronectin (MOMC) increases up to at least $6^{th}$ passage, the number of cells produced with type I collagen decreased by each passage (FIG. 2A). Further, as a result of analyzing the expression of various marker genes by RT-PCR method, it has been revealed that cells cultured on type I collagen do not express CD34, which is different from MOMC, and that expression of type I collagen and type III collagen was higher compared to MOMC (FIG. 2B). Further, by using a known culturing method that induces differentiation of MOMC into other cells to investigate the differentiation potential of cells cultured on type I collagen, it was shown that the cells produced with type I collagen did not differentiate into any cell (FIG. 2C), and it has been revealed that these cells have properties different from that of MOMC. From these results, it was shown that type I collagen does not have a MOMC differentiation-inducing potential, and that not only adhesion of cells to a culture plate, but a stimulation by a domain specific to fibronectin is necessary for differentiating $CD14^+$ monocytes into MOMC.

By considering that P stem cells that are taught in Patent Document 2 described in the Background Art are cells that can also be obtained from a culture on both collagen and fibronectin (see "Specific Example 3 of Example 1" of Patent Document 2), MOMC that cannot be at all obtained from a culture on collagen can be said to be an apparently different cell from P stem cell.

Example 3

Next, identification of adhesion molecule on monocytes associated with MOMC induction was attempted.

It is known that cell adhesion molecules binding with fibronectin are VLA-3, VLA-4 and VLA-5 of the integrin family. Among these, VLA-4 and VLA-5 are expressed in peripheral blood monocytes, while VLA-3 is not expressed (FIG. 3). Integrin is a heterodimer consisting of 2 subunits of α chain and β chain, VLA-4 consists of β chain (β1) and α chain (CD49d), and VLA-5 consists of β chain (β1) and α chain (CD49e). Thus, antibodies against CD49d and CD49e which are α chains constituting VLA-4 and VLA-5, respectively, were used to perform blocking, and adhesion molecule on monocytes associated with MOMC induction was identified. As a control, an antibody against CD49c which is the α chain of VLA-3 which is not expressed in monocytes was used.

Figure 4:
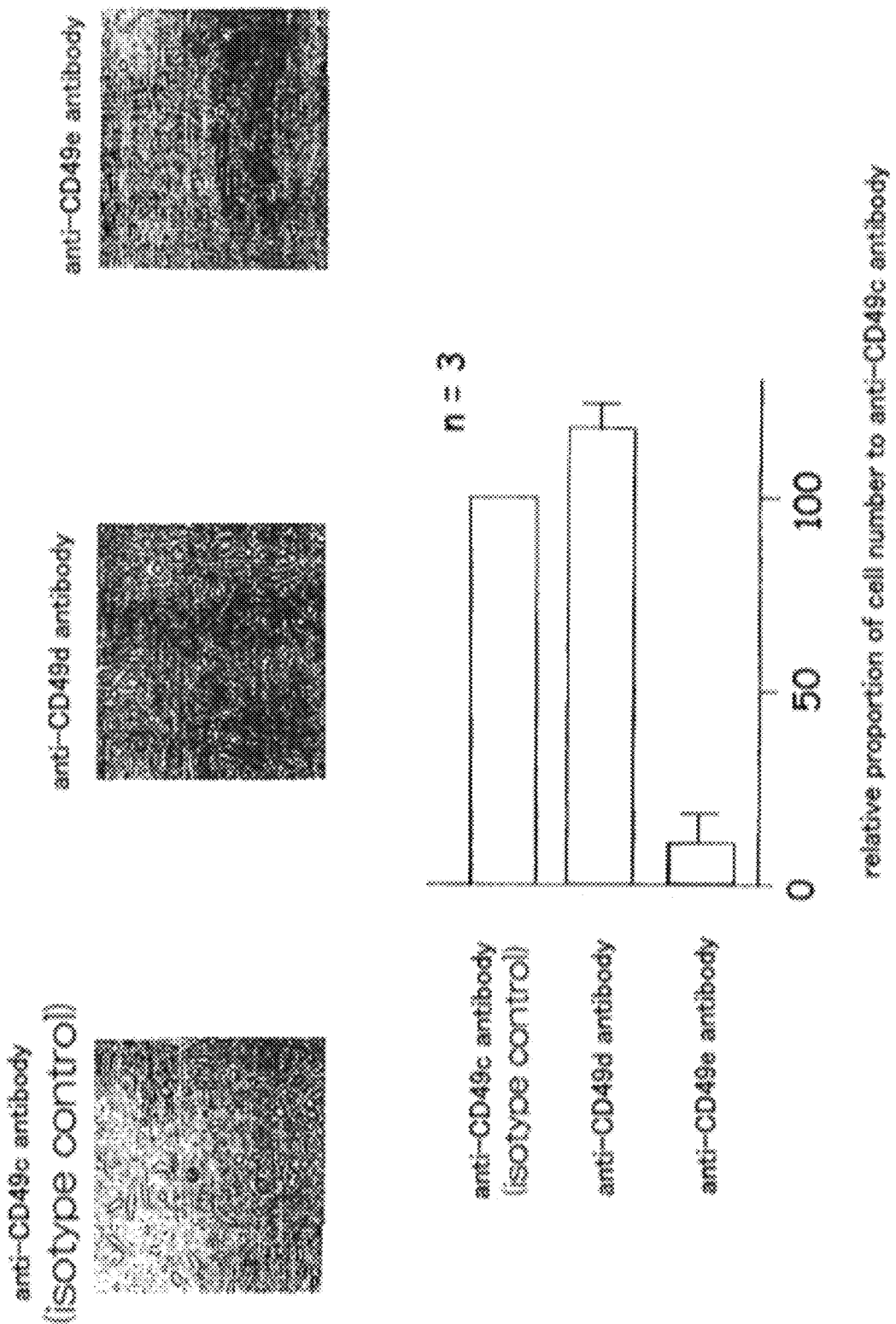
FIG. 4 It is a figure showing the results of comparative examination on MOMC differentiation potential, when integrin of a monocyte is blocked with an anti-CD49d antibody, anti-CD49e antibody, or anti-CD49c antibody.

Venous blood obtained from healthy adult donor was subjected to density-gradient centrifugation to isolate peripheral blood monocytes (PBMC). Then, the contaminating platelets were completely removed by using anti-CD61 antibody binding beads, and $CD14^+$ cells were isolated by using anti-CD14 antibody binding beads. The obtained $CD14^+$ monocytes were suspended on platelet culture supernatant containing MOMC differentiation-inducing factors, and inoculated on a fibronectin coated-plate at a cell density of $1\times10^6$/ml. The culture solution was added with anti-CD49d antibody (Beckman Coulter), anti-CD49e antibody (Beckman Coulter) or anti-CD49c antibody (Beckman Coulter) so that it becomes 20 µg/ml, respectively, and was cultured for 7 to 10 days. By counting and comparing the number of adhered cells on each plate at the end of the culture, the effect of various antibodies on MOMC differentiation induction was studied. As a result, when VLA-5 was blocked with anti-CD49e antibody, the induction of MOMC was significantly inhibited, and it has been revealed that the cell adhesion molecule associated with MOMC differentiation induction by fibronectin was VLA-5 (FIG. 4). On the other hand, as for cultured cells in which VLA-4 was blocked with anti-CD49d antibody, no difference was observed between the section added with anti-CD49c antibody as negative control, and it was shown that VLA-4 was not associated with MOMC induction (FIG. 4).

Example 4

Next, the fibronectin domain associated with MOMC induction was identified. As it is shown in FIG. 5, among the fibronectin domains, two domains, RGD and CS-1 were thought to be able to bind with VLA-5. Thus, competitive peptides against these RGD domain and CS-1 domain were added to the culture solution inducing MOMC, and the effect on MOMC induction was studied. As negative control, peptides wherein one amino acid of each competitive peptide was substituted to another amino acid were used (shown in SEQ ID NOs: 1 to 4).

Figure 6:
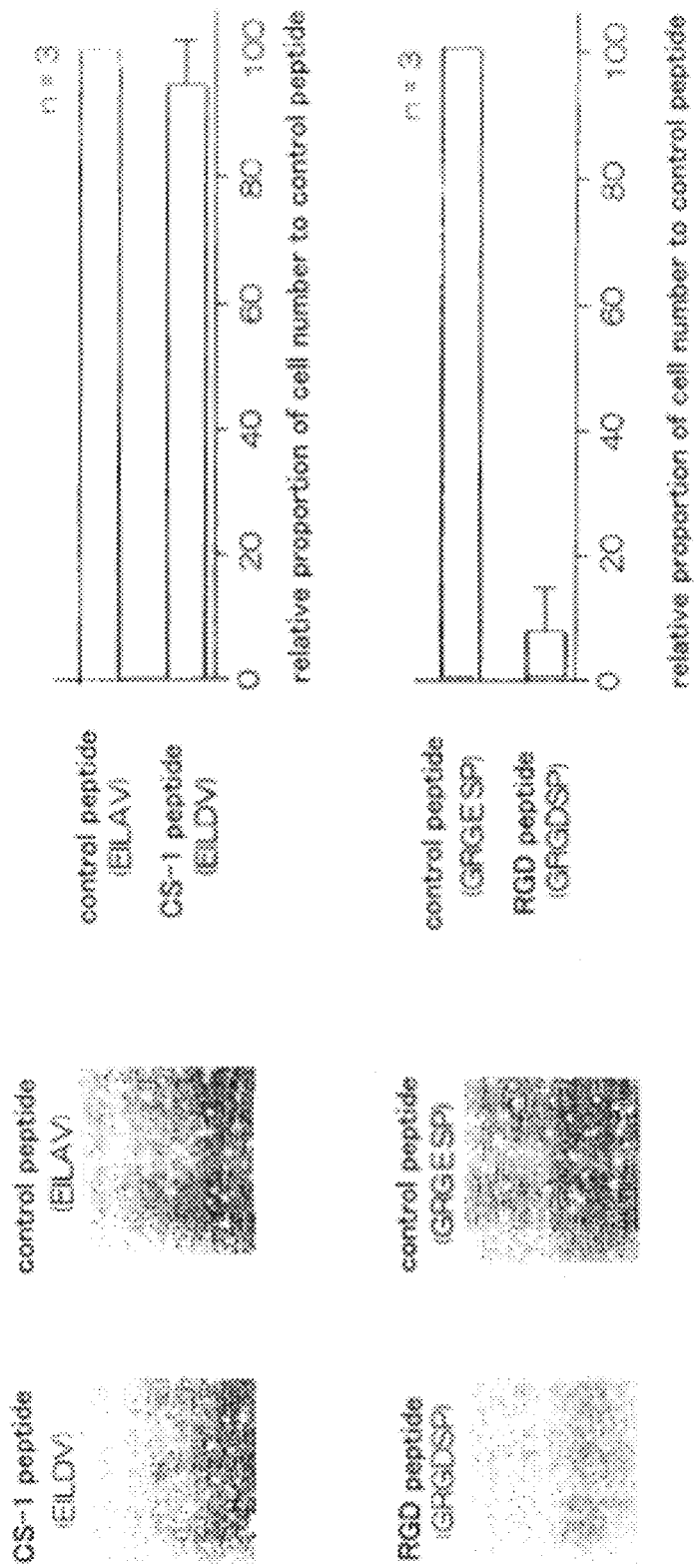
FIG. 6 It is a figure showing the change in MOMC differentiation efficiency, when a peptide competing with RGD or CS-1 domain of fibronectin is added.
Figure 8:
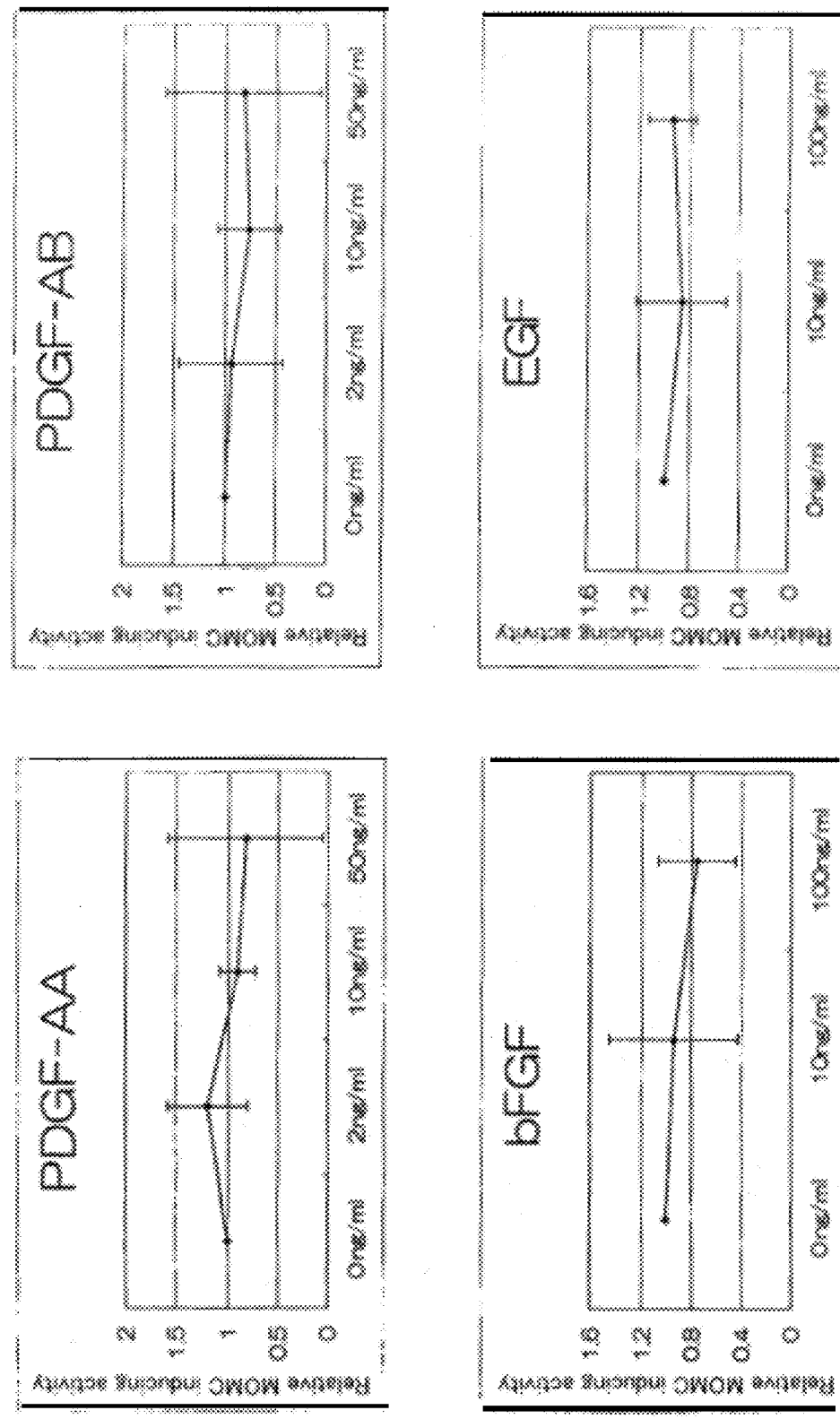
FIG. 8 It is a figure showing the investigation results on MOMC inducing activity of PDGF-AA, PDGF-AB, bFGF and EGF.

Venous blood obtained from healthy adult donor was subjected to density-gradient centrifugation to isolate peripheral blood monocytes (PBMC). The contaminating platelets were removed completely from the PBMC using anti-CD61 antibody binding beads, and CD14$^+$ monocytes were isolated by using anti-CD14 antibody binding beads. The obtained CD14$^+$ monocytes were suspended into platelet culture supernatant containing MOMC differentiation-inducing factors, and inoculated on a fibronectin-coated plate at a cell density of $1\times10^6$/ml. The culture solution was added with RGD peptide (GRGDSP; SEQ ID No: 1), CS-1 peptide (EILDV; SEQ ID No: 2), control peptide against RGD peptide (GRGESP; SEQ ID No: 3) or control peptide against CS-1 peptide (EILAV; SEQ ID No:4) so it becomes 500 µg/ml, and was cultured for 7 to 10 days. At the end of the culture, the number of adhered cells was counted, and by comparing the number of adhered cells added with competitive peptide and the number of adhered cells added with control peptide, the effect of each competitive peptide on MOMC differentiation induction was studied. As a result, almost no effect was observed when a peptide competing with CS-1 domain was added, while MOMC induction was significantly inhibited compared to control peptide when a peptide competing with RGD domain was added (FIG. 6). From these results, it has been revealed that RGD domain of fibronectin was associated with MOMC induction. More specifically, it has been suggested that RGD domain of fibronectin is deeply associated with the binding of VLA-5 and fibronectin, and that the binding of VLA-5 and fibronectin is inhibited in the presence of a competitive peptide of RGD domain and thus MOMC induction is inhibited.

Example 5

Identification of Liquid Factor Associated with MOMC Differentiation Induction

The present inventors have previously found out that it is necessary to coculture with platelets and not with lymphocytes for inducing differentiation of peripheral blood monocytes into MOMC (nonpatent document 5). The present inventors investigated the differentiation-inducing activity of 15 regulating factors (PDGF-AA, PDGF-AB, bFGF, EGF, IL-7, TGF-β, ENA78, GRO-α, IL-8, MIP-1α, NAP-2, PF-4, MCP-3, TARC, SDF-1). Among these 15 regulating factors, those other than SDF-1 are known as a regulating factor produced by platelets.

Venous blood obtained from healthy adult donor was subjected to density-gradient centrifugation to isolate peripheral blood monocytes (PBMC). Then, CD14$^+$ monocytes were isolated from the PBMC using anti-CD14 antibody binding magnetic beads. The obtained CD14$^+$ monocytes were suspended on a low glucose Dulbecco's modified Eagle's medium (DMEM) supplemented with 10% fetal bovine serum (FBS), and inoculated on a fibronectin-coated plate at a cell density of $2\times10^5$/ml. Each test substance was added to the culture solution so that it becomes a concentration of 0 to 100 ng/ml, and the mixture was cultured for 7 to 10 days. As a result, as it is shown in FIG. 7, it has been revealed that when 100 ng/ml of SDF-1 (R&D Systems) was added, MOMC-like spindle-shaped cells appeared at a high frequency (FIG. 7A), and that the induction activity into MOMC-like cells was concentration dependent (5, 10, 50, 100, 200 ng/ml) (FIG. 7B). On the other hand, any of the 14 regulating factors other than SDF-1 did not exert a differentiation-inducing activity into MOMC-like cells, and TGF-β, PDGF-AA, PDGF-AB and βFGF rather showed an activity of inhibiting induction into MOMC (FIGS. 8 to 11).

Example 6

Properties Identification of Spindle-Shaped Cells Induced by SDF-1

It was investigated whether the spindle-shaped cells which have been induced to differentiate by SDF-1 in Example 5 are MOMCs or not. First, the phenotype of the spindle-shaped cells was analyzed by flow cytometry and was shown to be CD14$^+$CD45$^+$CD34$^+$, and it has been clarified that the expression intensity of these molecules was equivalent to that of MOMCs induced by a conventional method (FIG. 12). Further, to confirm whether the spindle-shaped cells obtained by the present culturing method (using SDF-1 as inducing substance) were MOMCs having multidifferentiation potential or not, differentiation induction into cells shown in the following was performed.

Figure 13:
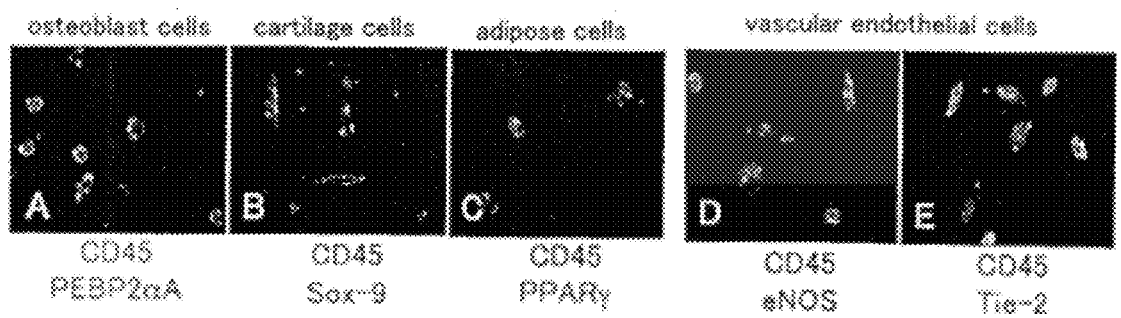
FIG. 13 It is a figure showing the examination results of multidifferentiation potential of MOMC-like spindle-shaped cells produced with SDF-1.

Spindle-shaped cells produced with SDF-1 were cultured according to the known culturing method for inducing differentiation of mesenchymal stem cells into osteoblast cells, cartilage cells and adipose cells, and the known culturing method for maintaining vascular endothelial cells (Arthritis Rheum 2001, 44, 1928-42; Circulation 2003, 108, 2511-16). After 1 week of culture, the morphology of the cultured cells was studied, and the expression of marker genes specific to each cell and CD45 was investigated by immunostaining method. The results are shown in FIG. 13. As marker genes used for assessing differentiation into each cell, PEBP2αA was used for osteoblast cells, SOX9 for cartilage cells, PPARγ for adipose cells, and eNOS and Tie-2 were used for vascular endothelial cells.

(1) Under a condition for differentiation into osteoblast cells, cells showed a generally round shape, and expression of PEBP2α A gene which is a specific transcriptional factor to osteoblast cells was observed after 1 week of culture. (FIG. 13A)

(2) Under a condition for differentiation into cartilage cells, cells were rich in cytoplasm, and showed a relatively large and generally round shape in morphology, and expression of Sox9 gene which is a specific transcriptional factor to cartilage cells was observed after 1 week of culture. (FIG. 13B)
(3) Under a condition for differentiation into adipose cells, fat droplets appeared, and expression of PPARγ2 gene which is a specific transcriptional factor to adipose cells was observed after 1 week of culture. (FIG. 13C)
(4) When the MOMC-like spindle-shaped cells were cultured under a known condition for maintaining vascular endothelial cells, they showed a polymorphism with small projections, and expression of eNOS gene and Tie-2 gene specific to vascular endothelial was confirmed (FIGS. 13D and E).

From the above results of (1) to (4), it has been revealed that the spindle-shaped cells induced by SDF-1 have a differentiation potential into osteoblast cells, cartilage cells, adipose cells, and vascular endothelial cells.

From the experimental results of Examples 5 and 6, it has been revealed that cells induced from $CD14^+$ monocytes by SDF-1: (1) display a spindle-shaped morphology, (2) are $CD14^+CD45^+CD34^+$, and (3) have a multidifferentiation potential. As these properties are in accordance with those of MOMC, it has been revealed that SDF-1 is a liquid factor having a MOMC differentiation-inducing potential.

Example 7

Effect of CXCR4 Expression Level in Peripheral Blood Monocytes on MOMC Differentiation Potential SDF-1 receptor is known to be a transmembrane-type chemokine receptor CXCR4. Thus, the present inventors studied whether the expression level of 4 chemokine receptors including CXCR4 and 1 cytokine receptor (LNGFR) on monocyte membrane affects the MOMC differentiation-inducing efficiency. The following chemokine receptors have been studied:
CXCR4 (SDF-1 receptor)
CCR1 (MIP1α, RANTES, MCP3, and MCP4 receptor)
CCR5 (MIP1α, MIP1β, RANTES, and MCP2 receptor)
CX3CR1 (Fractalkine receptor)
LNGFR (low affinity nerve growth factor receptor)

Figure 14:
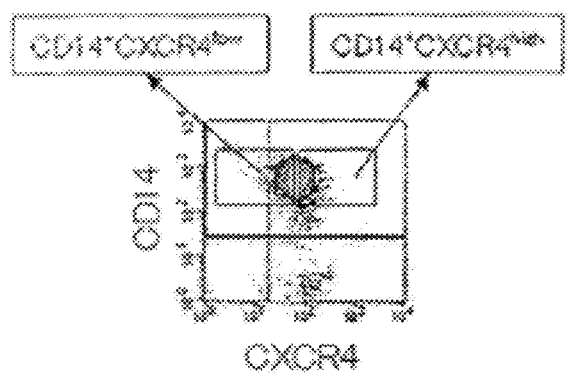
FIG. 14 It is a figure showing the investigation results of CXCR4 expression in CD14$^+$ monocyte population.

Venous blood obtained from healthy adult donor was subjected to density-gradient centrifugation to isolate PBMC. Then, $CD14^+$ monocytes were separated from the PBMC by using anti-CD14 antibody binding magnetic beads. The expression levels of CD14 in the obtained peripheral blood monocytes and each of the above-mentioned chemokine receptors were assessed by flow cytometry. As representative results, the results of flow cytometry assessment of CXCR4 expression are shown in FIG. 14.

Figure 15:
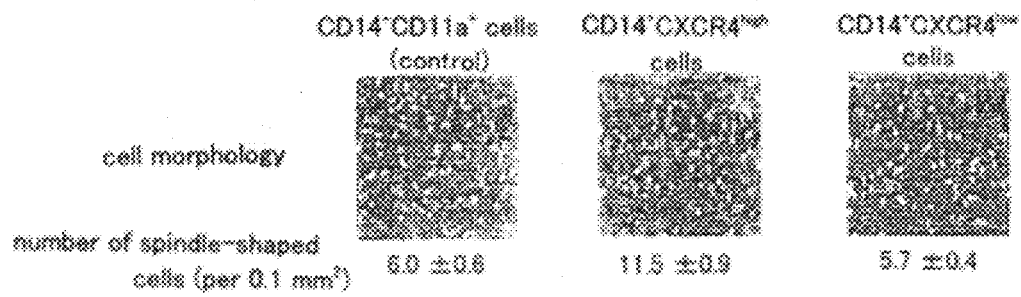
FIG. 15 It is a figure showing the results of comparative examination on differentiation efficiency of CD14$^+$CXCR4$^{low}$ cells and CD14$^+$CXCR4$^{high}$ cells into MOMC.
Figure 16:
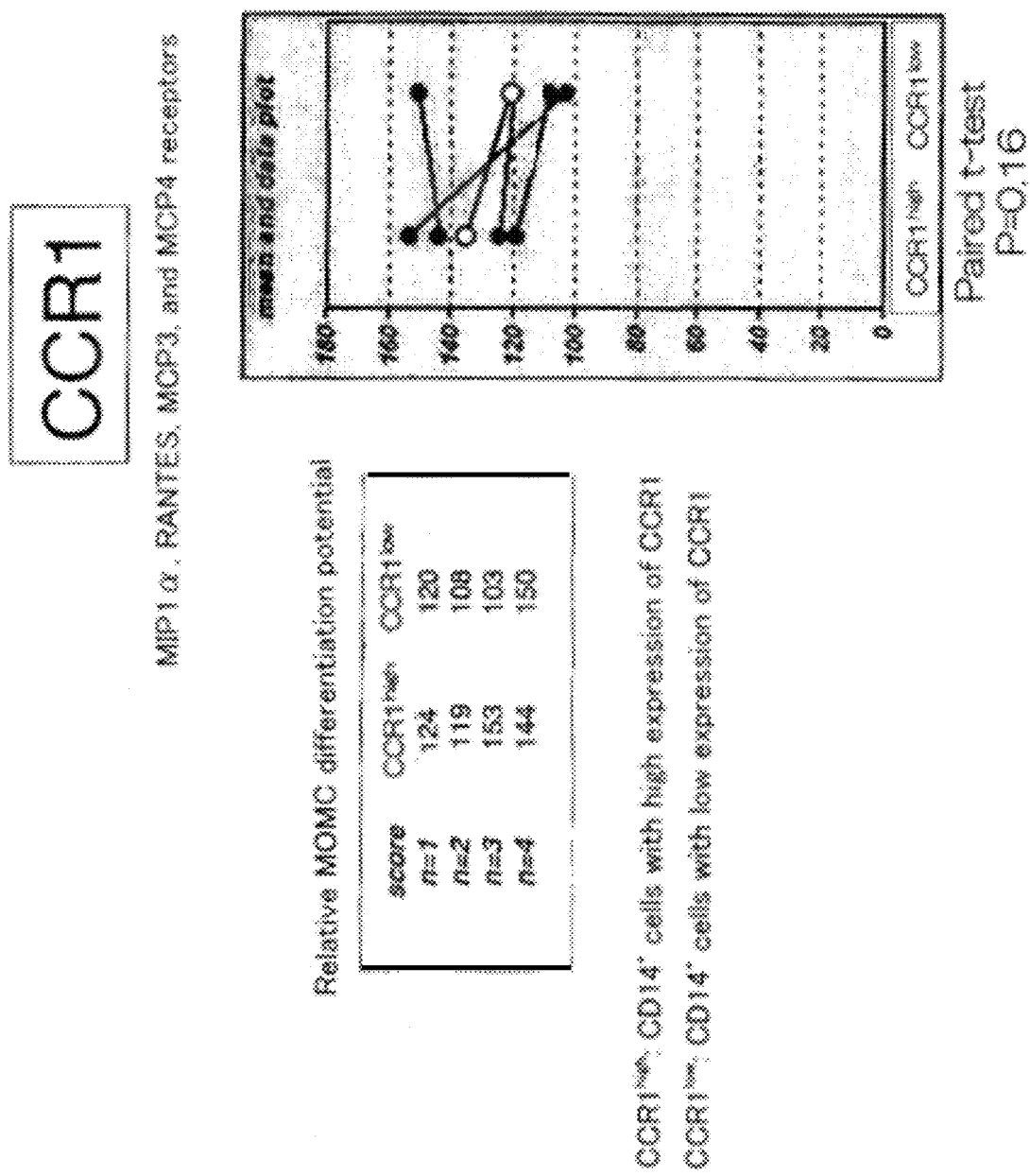
FIG. 16 It is a figure showing the results of comparative examination on differentiation efficiency of CD14$^+$CCR1$^{low}$ cells and CD14$^+$CCR1$^{high}$ cells into MOMC.
Figure 17:
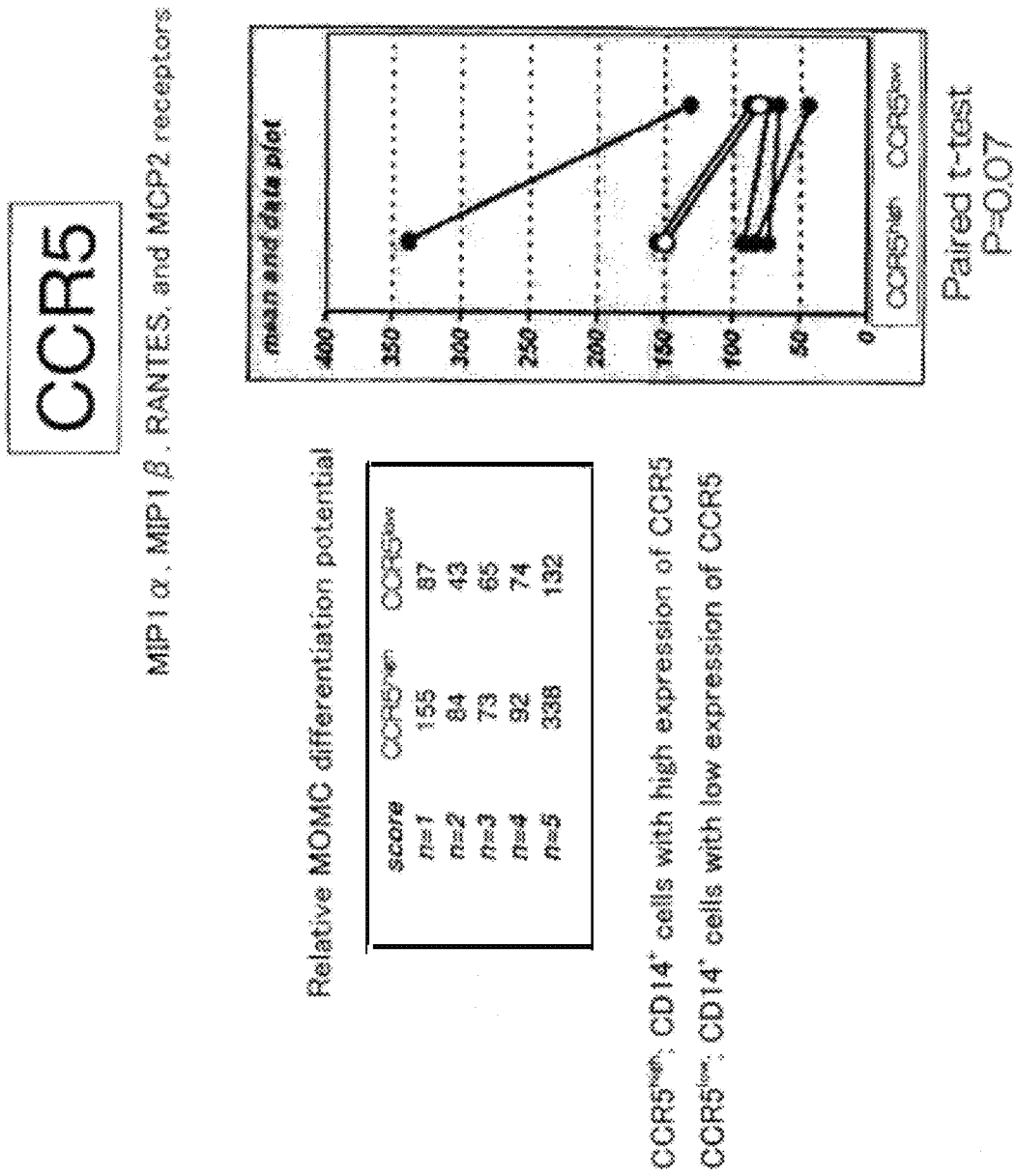
FIG. 17 It is a figure showing the results of comparative examination on differentiation efficiency of CD14$^+$CCR5$^{low}$ cells and CD14$^+$CCR5$^{high}$ cells into MOMC.
Figure 18:
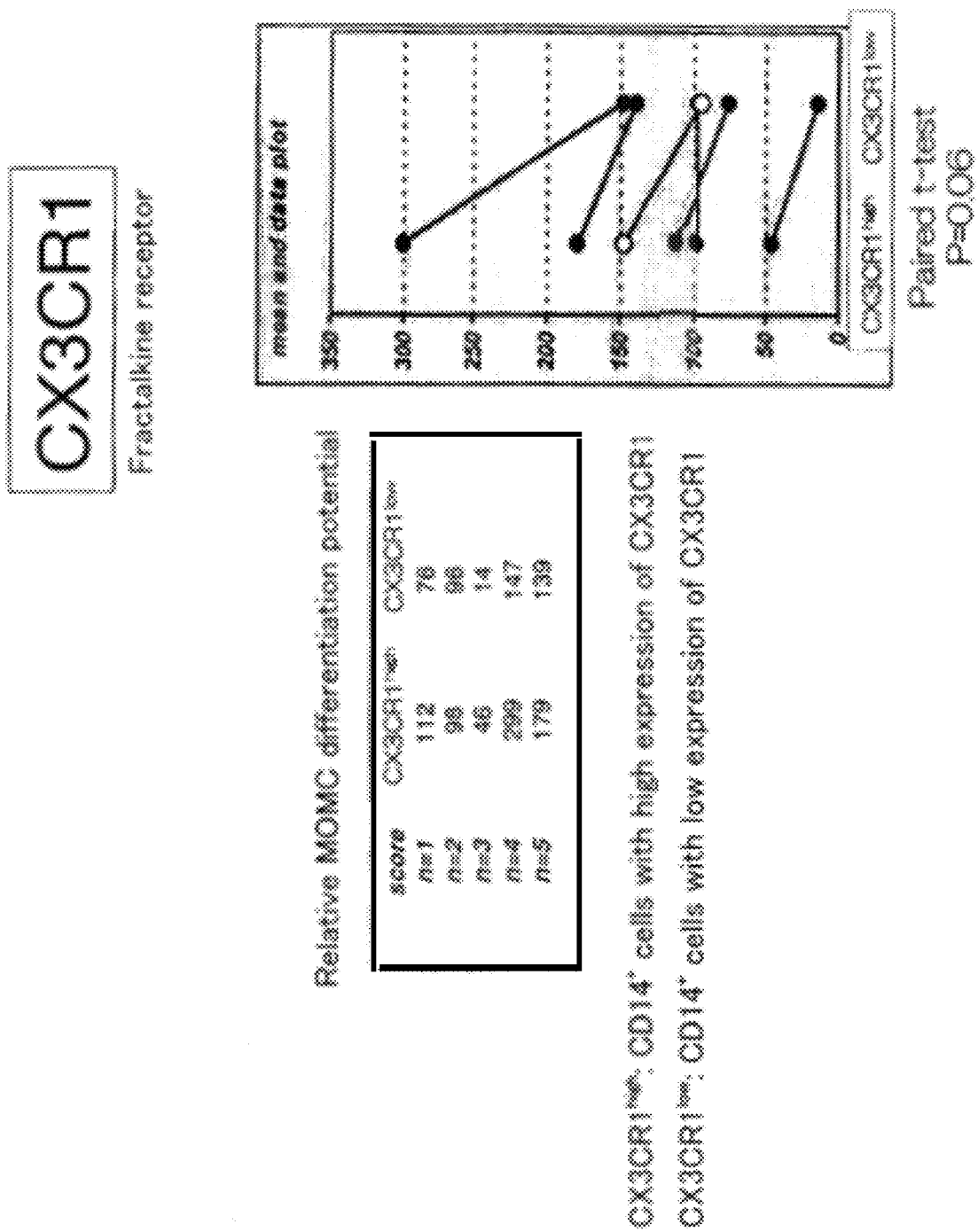
FIG. 18 It is a figure showing the results of comparative examination on differentiation efficiency of CD14$^+$CX3CR1$^{low}$ cells and CD14$^+$CX3CR1$^{high}$ cells into MOMC.

Further, by using flow cytometry, the above-mentioned $CD14^+$ monocytes were separated into a $CD14^+$ monocyte population with high expression of each of the above-mentioned chemokine receptors and a $CD14^+$ monocyte population with low expression of those chemokine receptors. Further, as a control, $CD14^+CD11b^+$ cell population was separated from the above-mentioned $CD14^+$ monocytes by using flow cytometry. Each cell population (cell cluster) was suspended into low glucose DMEM medium supplemented with 10% FBS, and then cocultured with platelets on a fibronectin-coated plate. After 7 to 10 days of culture, the number of spindle-shaped cells in each cell population was counted, and the differentiation potential into MOMC was compared. Concerning CXCR4 receptor, in the $CD14^+CXCR4^{low}$ cell population, the number of spindle-shaped cells per 0.1 mm$^2$ was similar to that of the control cell population (6.0±0.6), and was 5.7±0.4 (FIG. 15). However, the $CD14^+CXCR4^{high}$ cell population showed a significantly high level of 11.5±0.9 (FIG. 15). On the other hand, as it is shown in FIGS. 16 to 19, for chemokine receptors other than CXCR4, there was no relationship showing that MOMC differentiation potential is increased where these chemokine receptors are highly expressed. For example, for CCR1 and LNGFR, the MOMC differentiating potential was almost the same for the cells with a high expression of these chemokine receptors and the cells with a low expression of the same. For CCR5 and CX3CR1, cells with high expression of these chemokine receptors showed rather a low MOMC differentiation potential (not significant; P>0.05).

These results show that the MOMC differentiation potential of monocytes depends on the CXCR4 expression level, and supports that SDF-1/CXCR4 signal has a critical role in the MOMC induction by platelet-derived liquid factor.

From these results, it has been shown that 1) RGE domain in fibronectin is essential as adhesion factor; and 2) SDF-1 is essential as liquid factor, for inducing differentiation from peripheral blood monocytes into MOMC. Further, it has been revealed that 3) $CD14^+$ monocytes with high expression of CXCR4 have a high MOMC differentiation potential, and are cells that are suitable for producing MOMCs.

INDUSTRIAL APPLICABILITY

By using the method of the present invention, MOMCs can be produced more efficiently from peripheral blood monocytes, and it is possible to produce MOMCs at a lower cost. By inducing differentiation of the produced MOMCs into intended cells, it is possible to ensure stably cells for transplantation, and can greatly contribute to progress of regenerative medicine.

The invention claimed is:

1. A method for producing monocyte-derived multipotent cells (MOMCs) comprising culturing in vitro on fibronectin peripheral blood monocytes selected for expressing CD14 and for highly expressing CXCR4, wherein the in vitro culturing is performed in the presence of SDF-1.

* * * * *